(12) United States Patent
Poezevera

(10) Patent No.: US 6,890,306 B2
(45) Date of Patent: May 10, 2005

(54) ACTIVE MEDICAL DEVICE FOR THE DIAGNOSIS OF THE SLEEP APNEA SYNDROME

(75) Inventor: Yann Poezevera, Villeneuve Saint Georges (FR)

(73) Assignee: ELA Medical S.A., Môntrôuge (FR)

(\*) Notice: Subject to any disclaimer, the term of this patent is extended or adjusted under 35 U.S.C. 154(b) by 132 days.

(21) Appl. No.: 10/320,349

(22) Filed: Dec. 16, 2002

(65) Prior Publication Data

US 2003/0130589 A1 Jul. 10, 2003

(30) Foreign Application Priority Data

Dec. 14, 2001 (FR) .............................................. 01 16167

(51) Int. Cl.[7] .............................. A61B 5/08; A61B 5/05
(52) U.S. Cl. ........................ 600/533; 600/529; 600/547
(58) Field of Search ................................ 600/529, 532, 600/534, 537, 538, 547, 300, 301

(56) References Cited

U.S. PATENT DOCUMENTS

| | | | |
|---|---|---|---|
| 5,483,969 A | 1/1996 | Testerman et al. | .......... 128/716 |
| 6,045,514 A | \* 4/2000 | Raviv et al. | ................ 600/529 |
| 6,132,384 A | 10/2000 | Christopherson et al. | ... 600/529 |
| 6,138,675 A | 10/2000 | Berthon-Jones | ........ 128/204.23 |
| 6,342,039 B1 | \* 1/2002 | Lynn et al. | .................. 600/529 |
| 6,574,507 B1 | \* 6/2003 | Bonnet | ......................... 607/20 |

FOREIGN PATENT DOCUMENTS

| | | | | |
|---|---|---|---|---|
| EP | 970713 A1 | \* 1/2000 | .......... A61M/16/00 |
| EP | 0 970 713 A1 | 1/2000 | .......... A16M/16/00 |
| WO | WO 9924099 A1 | \* 5/1999 | .......... A61M/16/00 |
| WO | 99/65393 | 12/1999 | ............. A61B/5/08 |
| WO | WO 00/01438 | 1/2000 | .......... A61M/16/00 |

\* cited by examiner

*Primary Examiner*—Mary Beth Jones
*Assistant Examiner*—Navin Natnithithadha
(74) *Attorney, Agent, or Firm*—Orrick, Herrington & Sutcliffe LLP

(57) ABSTRACT

An active medical device have an improved diagnosis of a sleep apnea syndrome. This device measures the respiratory activity of the patient, determines a state of activity, this state being likely to take, according to satisfaction of predetermined criteria, a value representative of a state of sleep of the patient, and analyzes a detected signal corresponding to the respiratory activity to detect, when the aforementioned state is a state of sleep, the presence of respiratory pauses, and thereby to produce an indicating signal of sleep apnea in the event of the occurrence of a respiratory pause of duration longer than a first predetermined duration. The analysis also includes inhibiting the production of the aforesaid indicating signal, or a treatment to resolve an apnea, when the duration of the detected respiratory pause is longer than a second predetermined duration, typically of at least one minute.

9 Claims, 1 Drawing Sheet

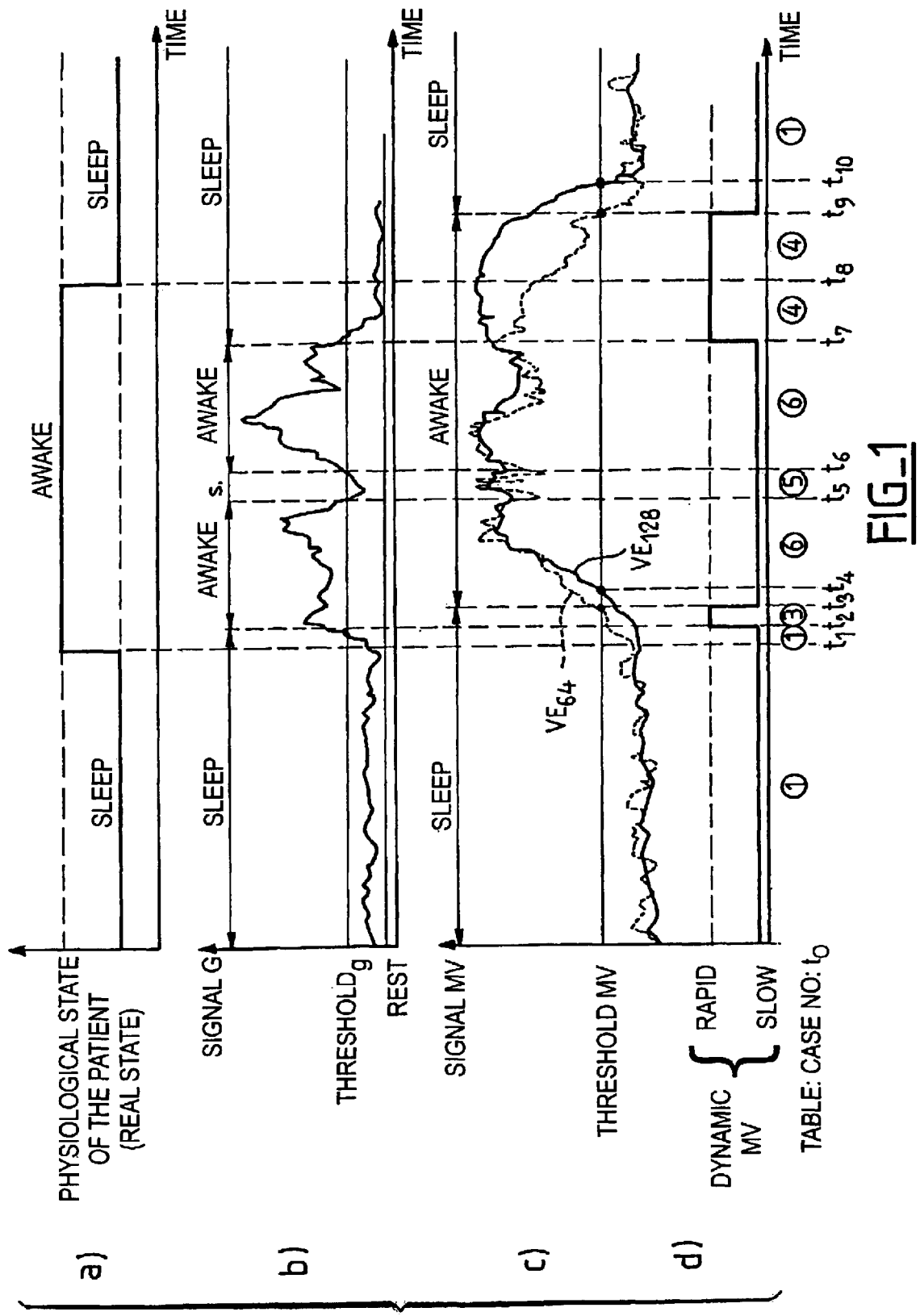

ACTIVE MEDICAL DEVICE FOR THE DIAGNOSIS OF THE SLEEP APNEA SYNDROME

FIELD OF THE INVENTION

The present invention relates to the diagnosis of the respiratory disorders, more particularly the diagnosis of the sleep apnea syndrome.

BACKGROUND OF THE INVENTION

The sleep apnea syndrome (SAS), more precisely the syndrome of obstructive apnea of sleep (SOAS) (as contrasted with the syndrome of central sleep apnea) is an affection generally caused by an obstruction of the respiratory tracts. It is susceptible to cause a certain number of disorders such as painful and insufficient breathing, heartbeat disturbance, and hypertension.

Various treatments of SOAS have been proposed including, for example, surgery, medications or maintenance of a positive pressure in the respiratory tracts by means of a facial mask applied during the sleep. It also has been proposed to treat SAS by neuro-muscular electric stimulation of the muscles controlling the air routes of the patient, as described in the U.S. Pat. No. 5,485,851 (to Medtronic, Inc.), and, more recently, by a particular stimulation of the myocardium (the so-called "electro-cardiac" stimulation) in the event of a detected SAS, as described, for example, in the U.S. Pat. No. 6,126,611 (to Medtronic, Inc.) and European patent application EO-A-0 970 713 and its corresponding U.S. Pat. No. 6,773,404. EP-A-0 970 713 (and U.S. Pat. No. 6,773,404) has the advantage of operating a discrimination between phases of awakening and sleep, in order to apply a therapy only during a phase of sleep, and to inhibit any treatment if the detected apnea occurs during a phase of awakening, because in this case it is normally not a pathological affection.

OBJECTS AND SUMMARY OF THE INVENTION

The present invention is directed to an improvement to the device described in EP-A-0 970 713 and its U.S. counterpart Pat. No. 6,773,404.

More precisely, the prior described and known device is an active medical device including means for measuring the respiratory activity of the patient, means for determining a state of activity, this state being likely to take, according to predetermined criteria, a value representative of a sleep state of the patient, and means for analyzing the signal delivered by the measuring means. The analyzing means is able to detect when the aforementioned state is a sleep state and the presence of respiratory pauses, and to produce an indicating signal of sleep apnea in the event of the occurrence of such a respiratory pause with a duration longer than a first predetermined duration.

The starting point of this invention is the observation, revealed at the time of clinical studies of the prior device, that in practice a system implementing a respiratory activity sensor based on a variation of pulmonary volume recorded at the thoracic level can, in certain circumstances, being deluded during the sleep phase in certain instances. One such delusion is caused by internal and physiological activity, for example, a shift in body position inducing a modification of volumes and/or position of the concerned organs, which interferes with the proper detection of the respiratory activity signal. A second delusion is caused by a clinical issue, for example, because of breathing that is exclusively abdominal in origin. Another delusion is external in origin, for example, because of momentary electromagnetic disturbances that interfere with respiratory activity detection.

In these particular situations, the device detects—wrongly—the occurrence of an apnea, i.e., a false positive, when the breathing is normal but was not diagnosed as such by the device.

It is an object of the present invention to minimize the risks of detection of such false positives by the medical devices equipped with such a means for detecting apnea, in particular sleep apnea. To this end, one aspect of the present invention is directed to a device of the known general type according to the above mentioned EP-A-0 970 713 and U.S. Pat. No. 6,773,404, wherein the improvement concerns providing the analyzing means with a means for inhibiting the production of the aforesaid indicating signal when the duration of the detected respiratory pause is longer than a second predetermined duration, preferably of at least one minute.

In a preferred embodiment, the device is an implantable device able to produce cardiac pacing stimulations as in a pacemaker or a defibrillator, a cardiovertor and/or a multisite device, including means for treating the sleep apnea syndrome by electro-cardiac stimulation, in which the treating means is inhibited when the duration of the respiratory pause is longer than the aforementioned second predetermined duration. In yet another embodiment, the device is an external device powered by line current or batteries, of the active medical device type.

BRIEF DESCRIPTION OF THE DRAWING

Further benefits, features and characteristics of the present invention will become apparent to a person of ordinary skill in the art in view of the following detailed description of the invention.

FIG. 1 illustrates a series of chronograms explaining the way in which discrimination between awakening and sleep is operated in accordance with a preferred embodiment of this invention.

DETAILED DESCRIPTION OF THE INVENTION

One now will describe an embodiment of an active medical device in accordance with an embodiment of the invention.

The respiratory activity of the patient is preferably analyzed according to the signal delivered by a minute ventilation sensor. Minute ventilation (also known as minute volume) ("MV") is a parameter that is obtained by a measurement of thoracic impedance, preferably an intrathoracic impedance, and known to be preponderantly physiological having a relatively slow variation over time.

The measurement of the minute ventilation is in itself well-known; it is operated between two electrodes laid out across the rib cage, or between an electrode (for example, a stimulation electrode if the implanted device has a cardiac stimulation function like a pacemaker) and the case of the implanted medical device. In the use of the implanted device, the impedance is measured by injection of a constant current of a few hundred microamperes, at a frequency of some Hertz, typically 8 Hz, and detection of a voltage between the electrodes. One suitable technique is described by Bonnet J L et al., Measurement of Minute-Ventilation with Different DDDR Pacemaker Electrode Configurations, *PACE*, Vol. 21, 98, Part 1, and is implemented in the cardiac treatment devices sold under the trademarks Chorus™ RM 7034 Talent™, and Symphony™ by the assignee of this invention of ELA Médical, Montrouge, France.

One can determine from this voltage signal representing the intrathoracic impedance a respiratory period defined as the lapse of time separating two peaks of the impedance signal. The peaks correspond to high impedances obtained at the time of the inspiration (when the lungs are filled with air). The decrease of the impedance corresponds to an expiratory phase.

The patients suffering from sleep apnea generally have normal expiratory phases, because the pulmonary pressure is sufficient to overcome the obstruction, but their inspiratory phases are abnormal because the lungs cannot properly fill with air. One then observes in this case a significant lengthening of the respiratory period. In a known manner, a sleep apnea is diagnosed when the following two criteria are cumulatively filled: First, there is an appearance of a respiratory pause of duration longer than 10 seconds, a phenomenon that is easy to detect by monitoring the minute ventilation signal; and Second, an occurrence of this respiratory pause during a phase of sleep of the patient, because an apnea in a state of awakening is not the cause of SAS.

The period of sleep is detected in an automatic manner, either starting from the signal delivered by the minute ventilation sensor, or by a separate sensor, for example, a sensor of patient activity measuring a parameter that is preponderantly physical, having a faster variation over time than minute ventilation, such as an acceleration sensor internal to the case, or by a combination of the signals delivered by these two types of sensor. One skilled in the art is referenced to a description of the prior known device in U.S. Pat. No. 6,773,404, which is incorporated herein by reference in its entirety, and in particular for one suitable manner of determining whether the patient is in a sleep state or an awakening state, although any useful technique for determining the state of the patient will be sufficient.

The reader is referred to European Patent Application EP-A-0 750 920 and its corresponding U.S. Pat. No. 5,722, 996, and EP-A-0 770 407 and its corresponding U.S. Pat. No. 5,766,228, also assigned herewith to Ela Médical, for additional details regarding the minute ventilation sensor and the activity acceleration sensors as may be employed in the present invention.

Regarding the determination of whether the patient is in a state of sleep or awakening, with reference to FIG. 1, the chronogram of line (a) represents the real physiological state of the patient, who is initially in a sleep phase (SLEEP). At the moment $t_1$ the patient awakens (AWAKE), and this awakening phase has a duration that ends at the moment $t_8$ when the patient enters a new sleep phase (SLEEP).

The chronogram of line (c) represents in full line the signal MV delivered by the minute-ventilation sensor MV, after the minute-ventilation measure was sampled and averaged over the 128 preceding respiratory cycles. This average value is indicated $VE_{128}$ The signal MV is a predominantly physiological parameter obtained by an intrathoracic impedance measurement. This measurement is preferably obtained between two electrodes laid out in the rib cage, or between an electrode (for example, a stimulation electrode, if the implanted device is a cardiac pacemaker) and the case of the device. The impedance is measured by injection of a constant current of a few hundred milliamperes, at a frequency of a few Hertz, typically 8 Hz, as previously described in Bonnet J L, et al.

The period of sleep is of course diagnosed in an automatic manner, typically starting from the signal delivered by the sensor that is monitoring the respiration rate of the patient. However, although the minute-ventilation signal is generally easiest to use for the monitoring of the respiration rate of the patient, other signals coming from other types of sensors can be used in the alternative to or to complement the use of the sensor MV, for example, a sensor of blood oxygen saturation.

In one known technique, the transition between awakening and sleep phases can be detected by comparing average value $VE_{128}$ with a threshold, indicated "Threshold MV", determined from an average value calculated over 24 hours of signal MV. Thus, in the illustrated example, the awakening of the patient was detected at the moment $t_4$ (reflecting a delay $t_4$-$t_1$ compared to the real moment of the awakening) and the falling-asleep at the moment $t_{10}$ (reflecting a delay $t_{10}$-$t_8$ compared to the real moment of falling asleep).

Advantageously, to reduce these delays in the detection of the phase shifts, an auxiliary sensor, preferably and typically an acceleration sensor ("sensor G") also is used. The signal delivered directly by the sensor G is then averaged over a relatively short duration (for example, 64 cardiac cycles) in order to eliminate artifacts and any short, non significant, variations. This averaged signal, indicated "signal G" is represented by the curve of the chronogram of the line (b) of FIG. 1. Signal G is then compared with an activity threshold, indicated "Threshold G", which, for example, is fixed at 10% above the value of the base line. The base line corresponds to a rest condition. If signal G exceeds Threshold G, one will define a state of the patient as being in an awakening phase according to the sensor G; in the contrary case, one will define the state as a sleep phase according to the sensor G. The device thus has two state indicators of awaking/sleep, defined starting from the two signals signal MV and signal G. These two states can be concordant or not.

The state of the patient being in an awakening or sleep phase continues to be diagnosed on the basis of signal MV but, according to the situation, the value having to be compared with Threshold MV will be either average $VE_{128}$ (referred to herein as the "slow dynamic") or average $VE_{64}$ calculated over a shorter period, typically over 64 preceding samples (referred to herein as the "fast dynamic").

The evolution of average $VE_{64}$ is illustrated in dotted lines on line (c) of FIG. 1, where one can see that the characteristic presents a form more variable than that of average $VE_{128}$ because the average taken over a shorter period has a larger variability. If the states (awake/sleep) given by the two signals, signal G and signal MV, agree, then the operation of the device is not modified, i.e., the state of awakening or sleep is given starting from signal MV by comparing $VE_{128}$ with Threshold MV (the slow dynamic).

On the other hand, in the event of discordance between the two signals (i.e., they do not produce the same phase), an additional criterion is introduced, which is the trend of the signal MV: decreasing, stable or increasing. This trend is determined by comparison between current value $VE_{128}$ and a value $VE_{128}$ previously calculated. The trend is known as stable if the variation is less than 10%, and otherwise it is deemed as increasing or decreasing, according to the sign of the variation.

When a change of state of the sensor G occurs, and the signal MV indicates an appropriate trend, the operation of the device is modified so as to determine the state as being in an awakening or sleep phase starting not from $VE_{128}$ (slow dynamic), but starting from $VE_{64}$ (fast dynamic) so as to get a greater reactivity. The cases where the dynamic is made fast are summarized by the state table below.

TABLE 1

| State Sensor MV | State Sensor G | Trend Signal MV | Dynamic | Case No. (FIG. 1) |
|---|---|---|---|---|
| Sleep | Sleep | — | Slow | 1 |
| Sleep | Awake | Decrease/Stable | Slow | 2 (not shown) |
| Sleep | Awake | Increasing | Fast | 3 |
| Awake | Sleep | Decreasing | Fast | 4 |
| Awake | Sleep | Increasing/Stable | Slow | 5 |
| Awake | Awake | — | Slow | 6 |

Referring to the example illustrated on FIG. 1, initially the sensor MV indicates a sleep phase ($VE_{128}$, Threshold MV); as long as the sensor G confirms this phase, the dynamic remains slow. At moment $t_1$, the patient awakes, but none of the two sensors (MV, G) yet crossed a threshold defining a change of state.

At moment $t_2$ the awakening phase is diagnosed by the sensor G, and as the trend of signal MV is increasing, the analysis of signal MV passes to a fast dynamic: it is the signal $VE_{64}$ (and no more $VE_{128}$) that is then compared with Threshold MV.

When, at moment $t_3$ $VE_{64}$ reaches Threshold MV, the two sensors each indicate a state of awakening phase, which is thus confirmed as such to the device, and the dynamic becomes again slow.

At the time of the episode between moments $t_5$ and $t_6$, which can, for example, correspond to a period of short rest, the sensor G indicates a of sleep phase (signal G passes again below Threshold G) but $VE_{128}$ thus remains higher than Threshold MV. As a result, the device continues to consider the state to be awakening and, trend MV not being decreasing, the dynamic remains unchanged (it remains slow).

The end of the awakening phase is characterized by a period of progressive rest of the patient that leads to the passing into the sleep phase at moment $t_8$. For this period of progressive rest, falling asleep is detected at moment $t_7$ by the sensor G, the trend MV signal being decreasing, and the dynamic becomes fast to be able to detect an apnea that could occur at the beginning of sleep, and being precise on the number of episodes. This fast dynamic is then maintained until confirmation of a sleep state, at moment $t_9$ by the sensor MV, corresponding to the crossing of Threshold MV by signal $VE_{64}$.

Ultimately, the detection of the awakening or sleep phases according to the invention makes it possible to advance the moment of detection of the awakening phase from $t_4$ (as obtained by the prior art) to $t_3$ (as obtained by the invention), and the detection of the sleep phase of $t_{10}$ (with the prior art) with $t_9$ (with the invention).

It will be noted that the use of signals $VE_{128}$ and $VE_{64}$ is not restrictive, and that it is equally possible to use signals $VE_{64}$ and $VE_{32}$ or $VE_{16}$, etc., in a comparable manner. In addition, it can be advantageous to envisage after each change of the dynamic a period of delay (for example, a duration of X respiratory cycles) or including a hysteresis loop, during which the dynamic is not modified, so as to avoid the undesirable phenomena of oscillations that might occur during changes of the dynamic.

In a manner characteristic of the invention, if during the detection of a series of apnea, one of the detected apnea presents an abnormally long duration, typically a duration greater than or equal to 1 minute, then it is considered that it is a false positive apnea. Consequently, the device will not take account of this apnea in its detection of the syndrome of the apnea. In other words, the control algorithm will not produce an indicating signal corresponding to an occurrence of a detected apnea. Nor, as the case might be, will the device apply a therapy: The algorithm will operate to inhibit any therapeutic treatment of SAS if such "a false positive apnea" is detected. It should be understood that in place of inhibiting an indicating signal, the control algorithm could simply disregard it in the case that the respiratory pause is longer than the second predetermined duration.

By eliminating the detection of a false apnea, another advantage is that the false apnea will not be taken into account in the calculation of an index of apnea (i.e., the number of apnea per hour of sleep).

Suitable devices for which the present invention has application include, but are not limited to, for example, the Chorus RM™, Talent™ and Symphony™ brand of implanted cardiac rhythm management devices available from Ela Médical, Montrouge, France. These devices are capable of receiving software instructions by telemetry, storing them in memory, and then executing those instructions to perform the functions described above in implementing the present invention, including the use of the minute ventilation signal acquired by the existing devices. The creation of suitable software instructions for controlling an implant to perform the aforementioned functions and algorithms of the present invention are believed to be within the abilities of a person of ordinary skill in the art.

The circuits for sensing a minute ventilation signal and an acceleration signal comprises substantially all of logic and hardware elements required to operate the sensors to sense the associated parameter and produce output signals corresponding to the sensed parameters, and to deliver signals utilizable by the main circuit of the implant. The main circuit includes a microprocessor and memory (RAM and/or ROM), as well as conventional latches, registers and power supplies (not shown) for processing the output signals provided by the respective sensors.

Furthermore, the preferred embodiment of the invention described herein is implemented in an architecture in which the means for performing the particular functions includes a microprocessor having associated software instructions stored in suitable memory devices, and analog and digital logic circuits for executing the software instructions that perform the described functions that are themselves known. Such an architecture is, for example, employed in the aforementioned devices manufactured by ELA Medical employing dual chamber cardiac pacing capabilities.

Although it does not present all of the advantages of the preferred solution with a microprocessor, a design in hard-wired discrete circuits having dedicated logic circuits for implementing the noted algorithms and control functions is nevertheless perfectly foreseeable, and equally within the framework of the present invention.

One skilled in the art will appreciate that the present invention can be practiced by other than the described embodiments, which are presented for purposes of illustration and not of limitation.

I claim:

1. An active medical device, comprising:
   means for detecting a respiratory activity of a patient and producing a signal corresponding to said detected respiratory activity;

means for determining a state of activity of the patient comprising means for acquiring an activity parameter, means for comparing said activity parameter to a predetermined criteria, and means for determining that said state is a sleep state on satisfaction of said predetermined criteria, means for analyzing the detecting means signal comprising means for identifying a respiratory pause and for determining a duration of said detected respiratory pause, and means for producing an indicating signal of sleep apnea in response to an identified respiratory pause having a duration longer than a first predetermined duration during a determined sleep state;

wherein the analyzing means further comprises means for inhibiting the production of the indicating signal in response to said respiratory pause duration being longer than a second predetermined duration.

2. The device of claim 1, wherein said second predetermined duration is at least one minute.

3. The device of claim 1, wherein said device is an implantable medical device and further comprises means for treating a sleep apnea syndrome by delivering an electro-cardiac stimulation in response to said indicating signal, and means for inhibiting said electro-cardiac stimulation treating means from delivering a stimulation in response to the detected respiratory pause being longer than said second predetermined duration.

4. An active medical device, comprising:

a respiratory activity monitor having an output signal corresponding to a patient's respiratory activity;

a patient state detector including an activity sensor having an output corresponding to a patient activity state, said detector including a predetermined criteria corresponding to a sleep state, and said output signal having a sleep state output in response to said patient activity signal satisfying said predetermined criteria;

a controller able to analyze the respiratory output signal and said state detector wherein the controller analyzes the respiratory output signal and identifies a respiratory pause therein and a duration of said detected respiratory pause, and produces an indicating signal of sleep apnea in response to an identified respiratory pause having a duration longer than a first predetermined duration during a determined sleep state;

wherein the controller operates to inhibit the production of the indicating signal in response to said respiratory pause duration being longer than a second predetermined duration.

5. The device of claim 4, wherein said second predetermined duration is at least one minute.

6. The device of claim 4, wherein said device is an implantable medical device and further comprises means for treating a sleep apnea syndrome by delivering an electro-cardiac stimulation in response to said indicating signal, and means for inhibiting said electro-cardiac stimulation treating means from delivering a stimulation in response to the detected respiratory pause being longer than said second predetermined duration.

7. An active medical device, comprising:

a respiratory activity monitor having an output signal corresponding to a patient's respiratory activity;

a patient state detector including an activity sensor having an output corresponding to a patient activity state, said detector including a predetermined criteria corresponding to a sleep state, and said output signal having a sleep state output in response to said patient activity signal satisfying said predetermined criteria;

a controller able to analyze the respiratory output signal and said state detector wherein the controller analyzes the respiratory output signal and identifies a respiratory pause therein and a duration of said detected respiratory pause, and produces an indicating signal of sleep apnea in response to an identified respiratory pause having a duration longer than a first predetermined duration during a determined sleep state;

wherein the controller operates to disregard the indicating signal in response to said respiratory pause duration being longer than a second predetermined duration.

8. The device of claim 7, wherein said second predetermined duration is at least one minute.

9. The device of claim 7, wherein said device is an implantable medical device and further comprises means for treating a sleep apnea syndrome by delivering an electro-cardiac stimulation in response to said indicating signal, and means for inhibiting said electro-cardiac stimulation treating means from delivering a stimulation in response to the detected respiratory pause being longer than said second predetermined duration.

* * * * *